United States Patent [19]

Osada et al.

[11] Patent Number: 4,541,718
[45] Date of Patent: Sep. 17, 1985

[54] PLASMA MONITORING METHOD AND PLASMA MONITOR

[75] Inventors: Hisajiro Osada, Tokyo; Yutaka Hiratsuka; Masahiro Watanabe, both of Yokohama, all of Japan

[73] Assignee: Hitachi, Ltd., Tokyo, Japan

[21] Appl. No.: 455,802

[22] Filed: Jan. 5, 1983

[30] Foreign Application Priority Data

Jan. 12, 1982 [JP] Japan .................... 57-2201

[51] Int. Cl.$^4$ .............................................. G01J 3/48
[52] U.S. Cl. .................................. 356/316; 356/417; 356/418
[58] Field of Search .............. 356/316, 417, 418, 306, 356/310

[56] References Cited

U.S. PATENT DOCUMENTS

| 2,734,418 | 2/1956 | Enns .................................. 356/307 |
| 3,298,275 | 1/1967 | DuBois et al. ..................... 356/306 |
| 3,744,918 | 7/1973 | Jacobsson ......................... 356/418 |
| 3,794,425 | 2/1974 | Smith et al. ...................... 356/418 |
| 4,164,373 | 8/1979 | Schuss et al. ..................... 356/316 |

FOREIGN PATENT DOCUMENTS 0207850 12/1982 Japan .................... 356/316

OTHER PUBLICATIONS

Masaharu Oshima, *Optical Spectroscopy in Reactive Sputter Etching and Its Application to Process Control*, Japanese Journal of Applied Physics, vol. 20, No. 4, Apr. 1981, pp. 683–690.

*Primary Examiner*—F. L. Evans
*Assistant Examiner*—S. A. Turner
*Attorney, Agent, or Firm*—Antonelli, Terry & Wands

[57] ABSTRACT

A plasma monitoring method and a plasma monitor in a dry process which utilizes a plasma. Among a large number of chemical species which constitute the plasma, one or two specified chemical species suited to grasp the situation of the dry process has/have its/their plasma light/lights detected so as to obtain the three-dimensional distribution of the densities of the single specified chemical species or the ratios of the two specified chemical species in the plasma.

11 Claims, 4 Drawing Figures

PLASMA MONITORING METHOD AND PLASMA MONITOR

BACKGROUND OF THE INVENTION

The present invention relates to a plasma monitoring method and a plasma monitor for measuring the distribution of the densities of a specified chemical species of molecules, atoms, ions or the like contained in a plasma, in a processing step utilizing the plasma such as sputtering and dry etching.

In the production of an LSI or a very LSI, it is required to arrange minute circuit pattens, the line widths of which are below several $\mu$m or below $\mu$m, at a high density. Therefore, wet processes such as plating and etching with a chemical solution are being switched over to dry processes capable of minute processing, such as dry etching and sputtering.

In order to precisely perform the minute processing with the dry process, it is necessitated to restrain fluctuations in processing conditions and to monitor the progress of the processing. To this end, several monitors have been proposed which monitor the progress of the processing by exploiting the light emission of a plasma generated during the dry process.

For example, in a monitor for dry etching, the quantity of light emission of the whole plasma generated during the processing and the quantity of light emission of an etching substance contained in the plasma are measured by individual measurement means, and the results are compared, whereby the density of the etching substance contained in the plasma is found so as to detect the end point of the etching.

In a monitor for sputtering, the quantities of light emission of two chemical species among chemical species constituting the plasma generated during the processing are measured by individual measurement means, and the results are compared, whereby the rate of the sputtering or the composition of a film to be formed is predicted.

Since these monitors measure the light emission of the whole plasma (or a part of the plasma) to be monitored, they merely grasp the state of the whole plasma (or the part of the plasma).

It is therefore impossible to grasp dispersion in the progress of the processing within a processing region. This signifies that, in the case of the dry etching, the degree of etching becomes excessive or insufficient, while in the case of the sputtering, dispersion in the thickness or composition of the formed film occurs inevitably. It is also impossible to obtain information for keeping the uniformity of processing within an identical lot or the reproducibility of a processed state among lots.

Further, since the two detection means are employed, the apparatus becomes high in cost and large in size. Another disadvantage is that errors develop due to the difference of the sensitivities of the respective detection means and the difference of the received quantities of light attributed to the difference of the positions where the respective detection means are arranged. The monitors have such numerous disadvantages.

SUMMARY OF THE INVENTION

An object of the present invention is to provide a plasma monitoring method which measures the distribution of the densities of a specified chemical species or the proportions of two specified chemical species in a plasma.

Another object of the present invention is to provide a plasma monitor which can measure the distribution of the densities of a specified chemical species or the proportions of two specified chemical species in a plasma.

Another object of the present invention is to provide a small-sized and inexpensive plasma monitor which can measure the distribution of the densities of a specified chemical species or the proportions of two specified chemical species in a plasma.

In order to accomplish the objects, according to the present invention, the measurement position of a plasma is successively selected. Plasma light from each measurement position is detected by spectroscopically dividing it into plasma light which has been emitted by all chemical species constituting the plasma, and plasma light which has been emitted by a specified chemical species contained in the plasma, or plasma light which have been emitted by two specified chemical species contained in the plasma. By comparing the detected results, the density of the specified chemical species or the proportion of the two specified chemical species at each measurement position is measured. Thus, the distribution of the densities or proportions of the specified chemical species in the plasma is obtained.

DESCRIPTION OF THE PREFERRED EMBODIMENT

Now, an embodiment of the present invention will be described with reference to the drawings.

Figure 1:
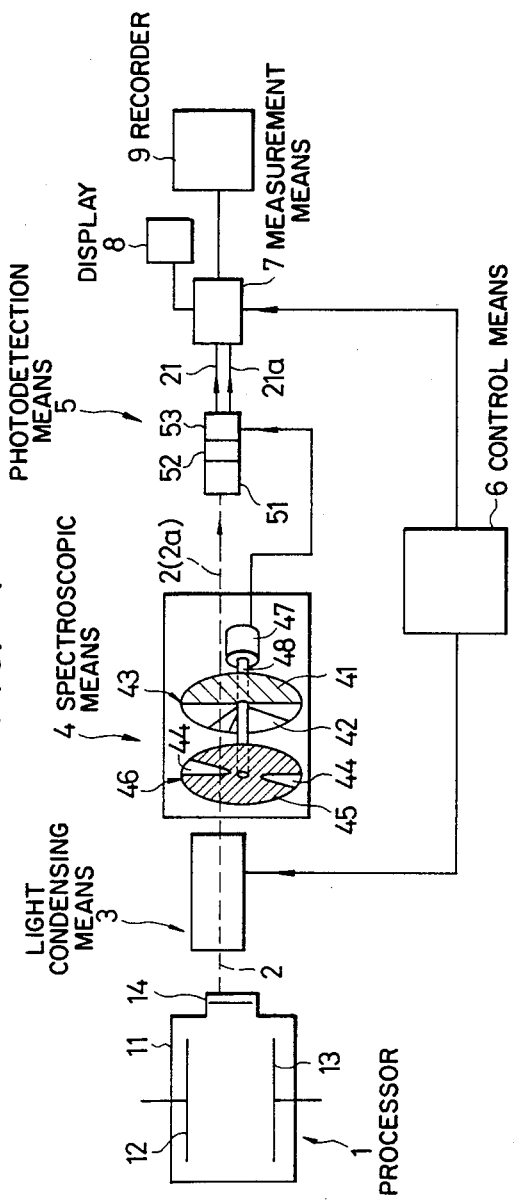
FIG. 1 is a block diagram showing the arrangement of a plasma monitor according to the present invention.

Referring to FIG. 1, a monitor for monitoring a plasma generated in a processor 1 is constructed of light condensing means 3 opposing to a window 14 of the processor 1, and for condensing plasma light 2 at a measurement position and emitting to a predetermined position; spectroscopic means 4 receiving the plasma light 2 emitted from the light condensing means 3, and for alternately taking out the entire plasma light 2 and plasma light of specified wavelengths 2a which is contained in the plasma light 2 and which is based on the light emission of a specified chemical species; photodetection means 5 for converting the plasma lights 2, 2a taken out by the spectroscopic means 4, into electric signals 21, 21a corresponding to the intensities thereof; control means 6 for instructing the light condensing means 3 the measurement position; measurement means 7 connected to the photodetection means 5 as well as the control means 6, and for comparing the electric signals 21, 21a applied from the photodetection means 5, so as to calculate the density of the specified chemical species in the plasma at the measurement position and to bring into correspondence this density and the signal of the measurement position applied from the control means 6; indication means, such as a display, 8 connected to the measurement means 7, and for indicating information on the measurement position given from the measurement means 7 and the density of the specified chemical species at this measurement position; and a recorder 9 connected to the measurement means 7, and for recording the information on the measurement position given from the measurement means 7 and the density of the specified chemical species at this measurement position.

Regarding the indication means 8 and the recorder 9, it is allowed to dispose only either of them.

The processor 1 comprises a pair of upper and lower electrodes 12 and 13 within an airtight vessel 11, and has a side wall formed with the window 14 for monitoring the interior. By applying a voltage across the electrodes 12 and 13 with a workpiece placed on the electrode 13, the plasma is generated between the workpiece and the electrode 12. This plasma emits the light.

Figure 2:
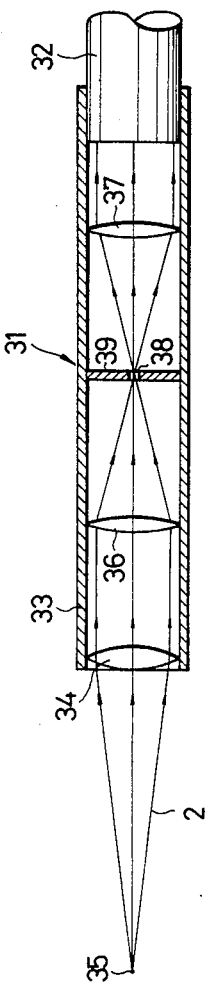
FIG. 2 is an enlarged partial sectional view showing the condensing optical system of light condensing means in FIG. 1.
Figure 3:
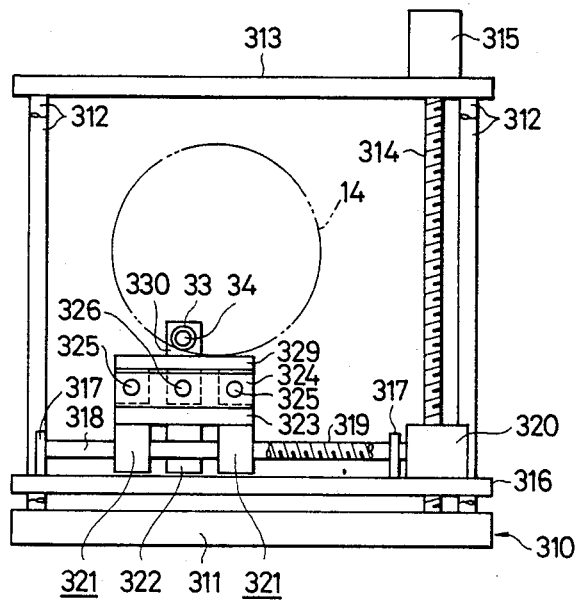
FIG. 3 is a front view showing the scanning mechanism of the light condensing means in FIG. 1.
Figure 4:
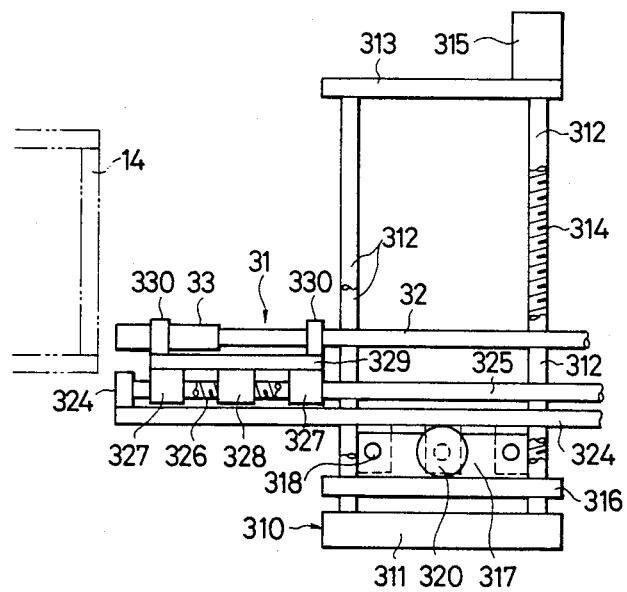
FIG. 4 is a side view corresponding to FIG. 3.

As shown in FIGS. 2 and 3, the light condensing means 3 is constructed of a condensing optical system 31 and a scanning mechanism 310.

The condensing optical system 31 is composed of optical fiber 32, a collimeter 33 which is snugly fitted on one end of the optical fiber 32, lenses 34, 36 and 37 which are supported within the collimator 33, and a partition plate 39 which is held between the lenses 36 and 37 so that a pinhole 38 may be located at the focal position of these lenses 36 and 37. The other end of the optical fiber 32 is connected to the spectroscopic means 4. In addition, the lens 34 has such a focal distance that, when the condensing optical system has come nearest to the window 14 of the processor 1, the focal point 34 of the lens 34 reaches the inner wall of the processor 1 opposite to the window 14.

The scanning mechanism 310 is carried on a base 311 with which the processor 1 is provided. Four guide bars 312 are erected on the base 311, and a top plate 313 is fixed to the upper ends of the guide bars. In addition, a first feed screw 314 is rotatably disposed between the base 311 and the top plate 313 in a manner to extend in parallel with the guide bars 312, and it is driven to rotate in the forward and reverse directions by means of a motor 315 which is supported on the top plate 313. A first movable base 316 arranged between the aforementioned base 311 and the top plate 313 is formed with holes in which the guide bars 312 are slidably fitted, and a threaded hole with which the feed screw 314 is in threadable engagement. Thus, the first movable base 316 is moved along the guide bars 312 by the rotation of the feed screw 314. On the carriage 316, a pair of guide bars 318 are fixedly supported by a pair of brackets 317. A second feed screw 319 is rotatably disposed between the two brackets 317 in a manner to extend in parallel with the guide bars 218, and it is driven to rotate in the forward and reverse directions by a motor 320 which is supported on the carriage 216. A second movable base 323 is fixed to bearings 321 which are slidably fitted on the guide bars 318, and a nut 322 with which the feed screw 319 is in threadable engagement. Thus, the second movable base 323 is moved in the horizontal direction by the rotation of the feed screw 319. The carriage 323 is formed to be sufficiently long in the direction perpendicular to the window 14 of the processor 1. On the carriage 323, a pair of guide bars 325 are fixedly supported by a pair of brackets 324 (one of which is not shown). A third feed screw 326 is rotatably disposed between the two brackets 324 in a manner to extend in parallel with the guide bars 325, and is driven to rotate in the forward and reverse directions by a motor (not shown) which is supported on the carriage 323. A third movable base 329 is fixed to bearings 327 which are slidably fitted on the guide bars 325, and a nut 328 with which the feed screw 326 is in threadable engagement. Thus, the third movable base 329 is moved perpendicularly to the window 14 by the rotation of the feed screw 326. The optical fiber 32 and collimator 33 of the condensing optical system 31 are supported on the carriage 329 through brackets 330 in such a manner that the lens 34 opposes to the window 14.

Owing to such construction, the collimator 33 of the condensing optical system 31 can be moved to any desired position within a plane parallel to the window 14 of the processor 1 by rotating the feed screws 314 and 319. The collimator 33 can also be moved to any desired position perpendicularly to the window 14 by rotating the feed screw 326. Accordingly, the focal point 35 of the lens 34 can be moved to any desired position within a range in which the window 14 of the processor 1 is perpendicularly extended. In the incident plasma light 2, a component arriving from the focal point 35 is collimated by the lens 34. The collimated beam is projected on the lens 36, which in turn condenses it and focuses it on the pinhole 38 of the partition plate 39 as the image of the focal point 35 of the lens 34. The plasma light 2 having passed through the pinhole 38 is collimated again by the lens 37, and the collimated beam is projected on the optical fiber 32.

At this time, that component of the plasma light 2 having entered the lens 34 which is other than the aforementioned component having arrived from the focal point 35 of the lens 34 is not collimated by passing through the lens 34. Therefore, when the collimated beam is condensed by the lens 36, such other component is condensed around the pinhole 38 and cannot pass through this pinhole. Accordingly, the plasma light having passed through the pinhole 38 consists only of the component having passed through the focal point 35 of the lens 34. By regarding it as the plasma light 2 arriving from the focal point 35 of the lens 34, the three-dimensional measurement of the plasma is permitted.

The spectroscopic means 4 is so constructed that a disc-shaped filter 43 and a disc-shaped mask 46 are integrally fixed to the rotary shaft 48 of a motor 47. The filter 43 consists of a filter portion 41 which allows only light of specified wavelength to pass therethrough, and several kinds of light-attenuating filter portions 42 which exhibit sligth wavelength selectivities and which have unequal light-attenuating efficiencies. The mask 46 is formed with portions 44 which transmit the plasma light 2, and a portion 45 which intercepts it.

The phases of the filter 43 and the mask 46 are so set at to attenuate the quantity of the plasma light 2 at a predetermined proportion in order that the detection accuracy of the photodetection means 5 may be prevented from lowering when the ratio between the intensities of the plasma light 2 condensed by the light condensing means 3 and the plasma light 2a of the specified chemical species contained in the plasma light 2 is large, that is, when the plasma light 2a of the specified chemical species is in an extremely small amount as compared with the plasma light 2.

Owing to such construction, the plasma light 2 projected from the light condensing means 3 passes through the mask 46 and reaches the filter 43 when the portion 44 of the mask 46 has traversed the optical axis of the means 3, and it is intercepted by the mask 46 and does not reach the filter 43 when the portion 45 has traversed the optical axis. When the filter portion 41 is traversing the axis of the plasma light 2 at the time of the arrival of the plasma light 2 at the filter 43, only the plasma light 2a of the specified wavelength in the plasma light 2 is transmitted to reach the photodetection means 5. On the other hand, when the light-attenuating filter portion 42 is traversing the axis of the plasma light 2, the plasma light attenuated at the predetermined proportion reaches the photodetection means 5. In this way, the plasma light 2 and the plasma light 2a of the specified chemical species contained in the former can be alternately derived.

The photodetection means 5 is constructed of a photoelectric transducer 51 which receives the plasma light 2 or 2a transmitted through the spectroscopic mens 4 and which produces an electric signal corresponding to the intensity of the plasma light 2 or 2a; an amplifier 52 by which the electric signal delivered from the photoelectric transducer 51 is amplified to an amplitude suitable for signal processing; and a discriminator circuit 53 which detects the rotational phase of the motor 47 (namely, the rotational phase of the filter 43 so as to discriminate whether the electric signal applied from the amplifier 52 is an electric signal 21 corresponding to the plasma light 2 or an electric signal 21a corresponding to the plasma light 2a.

The control means 6 gives rotation commands to the three motors 315, 320 and the other (not shown) of the light condensing means 3, to move the condensing optical system 31 to a required position. On the basis of the commands given to the respective motors 315, 320 and the other, it also supplies the measurement means 7 with the coordinates of the position of the focal point 35 of the lens 34 of the condensing optical system 31 with respect to the plasma in the processor 1 (that is, the coordinates of the measurement position).

In the above construction, the positions at which the plasma in the processor 1 is to be measured are set and are afforded to the control means 6 in advance. The light condensing means 3 is actuated by the commands of the control means 6 so as to locate the condensing optical system 31 to the first measurement position. When the plasma is generated and is emitting light in the processor 1 at this time, the plasma light 2 at the measurement position passes through the lens 34 and the collimator 33 to enter the optical fiber 32, and it is led to the spectroscopic means 4 by the optical fiber 32. When, at this time, the motor 47 is operating to rotate the mask 46 and the filter 43, the plasma light 2 is divided into the plasma light 2 attenuated at the predetermined proportion and the plasma light 2a of the specified wavelength (namely, the specified chemical species) contained in the received plasma light, and these lights are alternately projected from the spectroscopic means 4 to the photoelectric transducer 51. Then, the respective plasma lights 2 and 2a are converted into the electric signals corresponding to their intensities. After they are amplified by the amplifier 52, they are discriminated by the discriminator circuit 53 and are applied to the measurement means 7 as the electric signals 21 and 21a. Then, the measurement means 7 compares the electric signals 21 and 21a so as to find the density of the specified chemical species in the plasma at the measurement position. This density and the coordinates of the measurement position applied from the control means 6 to the measurement means 7 are applied to the indication means 8 and/or the recording means 9 and indicated and/or recorded.

The density distribution of the specified chemical species in the plasma can be obtained in such a way that the measurement position is successively moved on the basis of the commands of the control means 6, and that the densities of the specified chemical species in the plasma at the respective measurement positions are found.

When the filter 43 of the spectroscopic means 4 includes two sorts of filter portions 41 which transmit lights of unequal wavelengths, it becomes possible to detect the densities of two specified chemical species contained in the plasma.

As set forth above, according to the present invention, the distribution of the densities of a specified chemical species (for example, Al or AlCa in the etching of aluminum) in a plasma generated in a processor can be measured, so that a processing situation (for example, the end point of the aforementioned etching) can be precisely grasped. It is also possible to grasp a fluctuation in a processed state and to obtain information for properly performing the control of processing conditions.

In addition, since a single photodetection means suffices, no error develops in the photodetection means. Moreover, the apparatus can be made small in size as a whole and can be supplied inexpensively. The invention has such beneficial results.

We claim:

1. A plasma monitoring method comprising the step of condensing plasma light at a measurement position of a plasma, the measurement position being successively selected; the step of detecting the condensed plasma light at said each measurement position by spectroscopically dividing it into plasma light which is emitted by all chemical species constituting said plasma, and plasma light which is emitted by a specified chemical species contained in said plasma, the condensed plasma light being divided into plasma light emitted by all chemical species and by a specified chemical species using a single light filter with a plurality of filter portions; and the step of finding a density of the specified chemical species at said each measurement position on the basis of the divided plasma light detected by spectroscopically dividing the plasma light using the single light filter; thereby to measure a distributed state of the densities of said specified chemical species contained in said plasma.

2. A plasma monitoring method according to claim 1, wherein the condensed plasma light is spectroscopically divided using a mask and said filter, the mask and filter being so phased as to attenuate the quantity of plasma light for said specified chemical species and for all chemical species at predetermined proportions.

3. A plasma monitoring method comprising the step of condensing plasma light at a measurement position of a plasma, the measurement position being successively selected; the step of detecting the condensed plasma light at said each measurement position by spectroscopically dividing it into two sorts of plasma lights which are emitted by two specified chemical species among all chemical species constituting said plasma, the condensed plasma light being divided into one sort of plasma light emitted by one specified chemical species, and a second sort of plasma light emitted by a second specified chemical species, using a single light filter with a plurality of filter portions; and the step of finding a ratio between said two specified chemical species at said each measurement position on the basis of the two sorts of plasma lights detected by spectroscopically dividing the plasma light using the single light filter;

thereby to measure a distribution of the properties of said two specified chemical species in said plasma.

4. A plasma monitoring method according to claim 3, wherein the condensed plasma light is spectroscopically divided using a mask and said filter, the mask and filter being so phased as to attenuate the quantity of plasma light for the two sorts of plasma lights at predetermined proportions.

5. A plasma monitor comprising:

light condensing means including a condensing optical system which opposes to a window of a processor and which condenses plasma light at a measurement position in the processor through the window, said means selecting such measurement positions by moving said condensing optical system in three-dimensional directions relative to said window;

spectroscopic means for spectroscopically dividing the plasma light condensed by said light condensing means, into two sorts of plasma lights to-be-detected, said spectroscopic means including a rotatable single light filter having a plurality of filter portions, with the plurality of filter portions acting to divide the plasma light into the two sorts of plasma lights to-be-detected;

photodetection means alternately receiving the two sorts of plasma lights spectroscopically divided by said spectroscopic means, and for converting the received plasma lights into electric signals corresponding to intensities thereof, for amplifying the electric signals and for discriminating which of said two sorts of plasma lights said electric signals correspond to;

control means for instructing said light condensing means the measurement position of said plasma and for transmitting coordinate signals of said measurement position of said plasma;

measurement means connected to said photodetection means and said control means, and for measuring a specified chemical species on the basis of the two electric signals applied thereto from said photodetection means and for bringing into correspondence the measured result and said coordinate signals applied thereto from said control means; and displaying means and/or recording means constructed to said measurement means, and for displaying and/or recording said coordinates of said measurement position and said measured result which are applied thereto from said measurement means.

6. A plasma monitor according to claim 5, wherein said condensing optical system includes a collimator and lens means in said collimator, the collimator having a pinhole therein, the lens means being positioned such that light passing from the focal point of said lens means will pass through said pinhole while light passing from other locations will not pass through the pinhole, whereby three-dimensional measurement of the plasma can be achieved.

7. A plasma monitor according to claim 5, wherein said condensing optical system comprises optical fiber, a collimator which is disposed at an end part of said optical fiber on a light condensing side, and a lens which is disposed at an end part of said collimator on the light condensing side.

8. A plasma monitor according to claim 5, wherein said spectroscopic means includes a mask, which opens and closes an optical path of the plasma light emitted from said light condensing means, and said filter which spectroscopically divides the plasma light having passed through said mask into the two sorts of plasma lights to-be-detected, said mask and filter being supported on a rotary shaft of rotation driving means.

9. A plasma monitor according to claim 8, wherein the mask and filter are so phased as to attenuate the quantity of plasma light at predetermined proportions.

10. A plasma monitor according to claim 8, wherein said filter comprises a pair of filter portions each of which has a wavelength selectivity of allowing only plasma light of specified wavelength to pass therethrough.

11. A plasma monitor according to claim 8, wherein said filter comprises a filter portion which has a wavelength selectivity of allowing only plasma light of specified wavelength to pass therethrough, and a filter portion which has a slight wavelength selectivity and exhibits a light attenuating property.

* * * * *